United States Patent [19]

Mueller et al.

[11] Patent Number: 5,225,444
[45] Date of Patent: Jul. 6, 1993

[54] DISUBSTITUTED 4-HYDROXYPHENYLTHIO ANILIDES

[75] Inventors: Richard A. Mueller, Glencoe; Richard A. Partis, Evanston; James R. Deason, Wilmette, all of Ill.

[73] Assignee: G. D. Searle & Co., Chicago, Ill.

[21] Appl. No.: 750,810

[22] Filed: Aug. 27, 1991

Related U.S. Application Data

[63] Continuation of Ser. No. 606,028, Oct. 30, 1990, abandoned, which is a continuation of Ser. No. 76,583, Jul. 23, 1987, abandoned, which is a continuation of Ser. No. 809,965, Dec. 20, 1985, abandoned, which is a continuation-in-part of Ser. No. 698,049, Feb. 4, 1985, abandoned.

[51] Int. Cl.$^5$ ............... A61K 31/165; C07C 323/22
[52] U.S. Cl. ........................ 514/618; 514/617; 564/161; 564/162
[58] Field of Search ........... 564/161, 162, 168, 167; 514/618

[56] References Cited

U.S. PATENT DOCUMENTS

| | | | |
|---|---|---|---|
| 3,039,863 | 6/1962 | Fancher et al. | 71/2.6 |
| 3,392,194 | 7/1968 | Waring | 260/516 |
| 3,629,453 | 12/1971 | Waring | 424/320 |
| 3,652,646 | 3/1972 | Leigh et al. | 564/162 |
| 4,029,812 | 6/1977 | Wagner et al. | 424/298 |
| 4,076,841 | 2/1978 | Wagner et al. | 424/324 |
| 4,078,084 | 3/1978 | Wagner et al. | 424/324 |
| 4,153,803 | 5/1979 | Thiel et al. | 564/162 |
| 4,528,286 | 7/1985 | Moller | 514/232 |

FOREIGN PATENT DOCUMENTS

| | | |
|---|---|---|
| 1936463 | 9/1971 | Fed. Rep. of Germany . |
| 2716125 | 4/1977 | Fed. Rep. of Germany . |
| 141234 | 12/1978 | Japan . |
| 1064252 | 4/1967 | United Kingdom . |
| 1557622 | 6/1979 | United Kingdom . |

OTHER PUBLICATIONS

Samuelsson, "Leukotrienes: Mediators of Immediate Hypersensitivity Reactions and Inflammation", Science, V. 220, 1983, pp. 568-575.
Bach, "Inhibitors of Leukotriene Synthesis and Action", The Leukotrienes, Chemistry and Biology, Academic Press, pp. 163-194.
Lee, et al., "Human Biology and Immunoreactivity of Leukotrienes" Advances in Inflammation Research, vol. 6, pp. 219-225, Raven Press (1984).
Editorial, "Leukotrienes and other Lipoxygenase Products in the Pathegonesis and Therapy of Psoriasis and Dermatoses", Arch. Dermatol., vol. 119, pp. 541-547, (Jul. 1983).
Lewis, et al., "A Review of Recent Contributions on Biologically Active Products of Arachidonate Conversion", Int. J. Immunopharm vol. 4, No. 2, pp. 85-90, (1982).
Bach, "Prospects for the Inhibition of Leukotriene Synthesis", Biochemical Pharmacology, vol. 33, NO. 4, pp. 515-521 (1984).
Becker, "Chemotactic factors of Inflammation", pp. 223-225, (Elsevier Science Publishers B. V. Amsterdam, 1983).
Sharon, et al., "Enhanced Synthesis of Leukotriene B$_4$ by Colonic Mucosa in Inflammatory Bowel Disease" Gastroenterology, vol. 86, pp. 453-460, (1984).
Musch, et al., "Stimulation of Colonic Secretion by Lipoxygenase Metabolities of Arachidonic Acid", Science, vol. 217, p. 1255 (1982).
Harvey, et al., "The Preferential Inhibition of 5-Lipoxygenase Product Formation by Benoxaprofen", J. Pharm. Pharmacol., vol. 35, Chem. Abst. 90:151802x, vol. 90 (1979) (Tsuda).
Khim. Tekhnol. 20(4), pp. 568-574 (1977).
Pestic. Biochem. Physiol, 12(1), 23-30 (1979).

Primary Examiner—Carolyn Elmore
Assistant Examiner—Shailendra Kumar
Attorney, Agent, or Firm—Mary Jo Kanady; Paul D. Matukaitis

[57] ABSTRACT

The compounds of this invention are anilides represented by the formula:

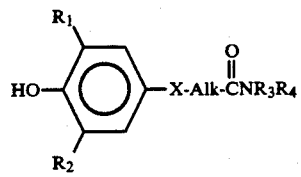

wherein: $R_1$ and $R_2$ are the same or different members of the group consisting of halo, phenyl, substituted phenyl and a

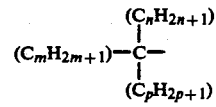

group wherein n, m and p are independently an integer of from 1 to 8 provided that $n+m+p$ is equal to or less than 10; X is thio, sulfinyl or sulfonyl; Alk is straight or branched chain lower alkylene; $R_3$ is hydrogen or lower alkyl; and $R_4$ is phenyl or substituted phenyl. The compounds of the present invention are useful in the treatment of inflammation, allergy and hypersensitivity reactions and other disorders of the immune system.

13 Claims, No Drawings

DISUBSTITUTED 4-HYDROXYPHENYLTHIO ANILIDES

This application is a continuation of U.S. application Ser. No. 07/606,028 filed Oct. 30, 1990, now abandoned, which is a continuation of U.S. application Ser. No. 07/076,583 filed Jul. 23, 1987, now abandoned, which is a continuation of U.S. application Ser. No. 06/809,965 filed Dec. 20, 1985, now abandoned, which is a continuation-in-part of U.S. application Ser. No. 06/698,049 filed Feb. 4, 1985, now abandoned. U.S. application Ser. No. 07/558,965 filed Jul. 27, 1990, now abandoned is a related case.

BACKGROUND OF THE INVENTION

A. Field of the Invention

The present invention relates to novel anilides and more particularly relates to anilides which are 5-lipoxygenase inhibitors and are useful as anti-inflammatory and anti-allergy agents.

It is well recognized that arachidonic acid and its analogs, unsaturated fatty acids, are the precursors of prostaglandins, thromboxanes, the 5-, 11-, 12- and 15-hydroxyeicosatetraenoic acids (HETEs, DIHETEs, TRIHETEs) and hydroperoxyeicosatetraenoic acids (HPETEs) and the leukotrienes, all of which have profound physiological effects. The leukotrienes, which are produced via the 5-lipoxygenase pathway, are the major contributors to the onset of the symptoms of asthma, and mediators for immediate hypersensitivity reactions and inflammation.

Leukotrienes are found in inflammatory exudates and are involved in the process of cellular invasion during inflammation. The term "leukotrienes" is used as a generic term to describe a class of substances, such as slow-reacting substance (SRS) which is an important mediator in asthma and other immediate hypersensitivity reactions. Immunologically generated SRS is usually referred to as slow-reacting substance of anaphylaxis (SRS-A). SRS-A consists of leukotrienes (LT) known as $A_4$, $B_4$, $C_4$, $D_4$, $D_5$ and $E_4$. $LTC_4$ is at least 100 times more potent than histamine in causing long lasting bronchoconstricting effects. The leukotrienes also increase vascular permeability and cause decreased cardiac output and impaired ventricular contraction. $LTB_4$ may be an important mediator of inflammation in inflammatory bowel disease.

Chemotaxis is a reaction by which the direction of migration of cells is determined by substances in their environment. It is one of the major processes bringing leukocytes from the blood to an inflammatory site, whether the inflammation is caused by an infectious agent, allergic challenge, or other pro-inflammatory stimuli. $LTB_4$ is not only chemotactic for neutrophils and monocytes, but is also highly active in stimulating eosinophil locomotion. The infiltration of eosinophils is one of the histologic features of a variety of allergic reactions.

With the exception of benoxaprofen, which has 5-lipoxygenase inhibition activity, aspirin and the other non-steroidal anti-inflammatory agents (NSAIDs) such as indomethacin, ibuprofen, fenoprofen, and the like, inhibit the synthesis of prostaglandins via the cyclooxygenase pathway of arachidonic acid. These prostaglandin synthetase inhibitors generally exhibit anti-inflammatory, anti-pyretic and analgesic activity, and are widely used in the treatment of arthritis. The non-steroidal anti-inflammatory agents can lead to the formation of additional pro-inflammatory derivatives of arachidonic acid produced through the 5-lipoxygenase pathway which play a role in immediate hypersensitivity reactions and also have pronounced pro-inflammatory effects. Administration of the NSAIDs alone can produce allergic reactions including bronchospastic reactivity; skin rashes; syndrome of abdominal pain, fever, chills, nausea and vomiting, and anaphylaxis. For this reason, aspirin and the other non-steroidal anti-inflammatory agents (NSAIDs) are generally contraindicated for patients suffering from asthma or who have previously exhibited allergic sensitivity to aspirin or other NSAIDs.

Prior to the recognition of the arachidonic acid cascade and the significance and interaction of the 5-lipoxygenase and other arachidonic acid cascade conversion products in allergic reactions and inflammation, the search for effective therapeutic agents was based primarily on those agents which treated the symptoms of allergy and inflammation. There has since been effort to develop new drugs which selectively block the formation of the mediators of these conditions, and the present invention provides (phenylthio)anilides which are metabolically stable inhibitors of the 5-lipoxygenase pathway and are useful in the treatment of asthma and other allergy and hypersensitivity reactions, and many types of inflammation.

To date, benoxaprofen has been the only commercial anti-inflammatory agent which has 5-lipoxygenase inhibition activity. Prior to its withdrawal from the market because of untoward side effects, benoxaprofen was considered to represent a significant advance in the treatment of crippling arthritis and psoriasis. Thus, there remains a longstanding need for agents which block the mechanisms responsible for inflammation and allergic reactions, and which can be safely employed to treat, for example, arthritis, asthma, psoriasis and other dermatoses, allergic reactions and other 5-lipoxygenase mediated conditions. A need also exists for agents which can be administered with the inhibitors of other lipoxygenase enzymes, e.g. cyclooxygenase, to mitigate their side effects and support their desirable medicinal properties.

See Bengt Samuelson, "Leukotrienes: Mediators of Immediate Hypersensitivity Reactions and Inflammation", *Science*, Vol. 220, pp. 568–575 (May 1983); Michael K. Bach, "Inhibitors of Leukotriene Synthesis and Action", *The Leukotrienes, Chemistry and Biology*, pp 163–194 (Academic Press, Inc., 1984); C. W. Lee et al., "Human Biology and Immunoreactivity of Leukotrienes", *Advances in Inflammation Research*, Volume 6, pp 219–225 (Raven Press, New York, 1984); Editorial, "Leukotrienes and other Lipoxygenase Products in the Pathegonesis and Therapy of Psoriasis and Dermatoses", *ArcL. Dermatol.* Vol. 119, pp 541–547 (July, 1983); Robert A. Lewis et al., "A Review of Recent Contributions on Biologically Active Products of Arachidonate Conversion", *Int. J. Immunopharmac* Vol. 4, No. 2, pp 85–90 (1982); Michael K. Bach, *Biochemical Pharmacology*, Vol. 23, No. 4, pp 515–521 (1984); E. L. Becker, *Chemotactic Factors of Inflammation.* pp 223–225 (Eliver Science Publishers B. V., Amsterdam, 1983); P. Sharon and W. F. Stenson, *Gastroenterology* Vol. 84, 454 (1984); and M. W. Musch, et al., *Science.* Vol. 217, 1255 (1982).

The present invention provides compounds which block the 5-lipoxygenase pathway of the arachidonic acid cascade, block the formation of the leukotrienes therefore responsible for the allergy and inflammation, and hence and represent a new class of therapeutic agents which are useful in the treatment of allergic and hypersensitivity reactions and inflammation, alone, or in combination with other oxygenase inhibitors such as the non-steroidal anti-inflammatory agents (cyclooxygenase inhibitors).

B. Prior Art

Wagner et al. U.S. Pat. No. 4,029,812, and related U.S. Pat. Nos. 4,076,841 and 4,078,084, which issued from divisional applications to the -812 application all assigned to The Dow Chemical Company, disclose 2-(3,5-di-tert-butyl-4-hydroxyphenyl)thiocarboxylic acids, esters and simple amides which are hypolipidemics and are useful in reducing plasma lipid levels, especially cholesterol and triglyceride levels.

The Wagner et al. and related compounds have also been reported in the literature as plasticizers and pesticides. See for Example: Izv. Vyssh. Uchebn. Zaved., Khim. Khim. Tekhnol. 20(4), 568-574 (1977); *Pestic. Biochem. Physiol.* 1979, 12(1), 23-30. *Chem. Abs.* 90(19):151802x is of interest.

SUMMARY

The compounds of this invention are anilides represented by the formula

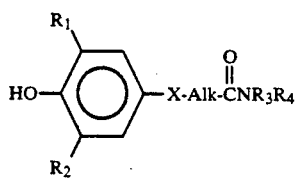

wherein: $R_1$ and $R_2$ are the same or different members of the group consisting of halo, phenyl, substituted phenyl and a

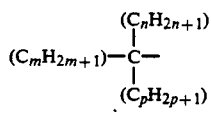

group wherein n, m and p are independently an integer of from 1 to 8 provided that $n+m+p$ is equal to or less than 10; X is thio, sulfinyl or sulfonyl; Alk is straight or branched chain lower alkylene; $R_3$ is hydrogen or lower alkyl; and $R_4$ is phenyl or substituted phenyl.

The compounds of the present invention are useful in the treatment of allergy and hypersensitivity reactions and inflammation. The compounds are particularly useful in the treatment of arthritis and other inflammatory joint disease, asthma/ proliferative skin disease such as psoriasis, and the like, alone or in combination with one or more cyclooxygenase inhibitors.

DETAILED DESCRIPTION OF PREFERRED EMBODIMENTS

The compounds of the present invention are generally administered in oral or parenteral dosages of from 0.1 to 100 mg/kg, preferably 0.5 to 50 mg/kg daily, preferably in divided dosages, to patients suffering from allergic or hypersensitivity reactions or inflammation, and are preferably applied topically to patients suffering from proliferative skin disease such as psoriasis. The compounds may be administered as the sole therapeutic agent, or in combination with other agents such as cyclooxygenase inhibitors, particularly in patients who exhibit pro-inflammatory or allergic response to, for example, conventional non-steroidal anti-inflammatory agents. Parenteral, e.g., intravenous, administration is preferable if a rapid response is desired, as, for example, in some cases of asthma.

Generally speaking, synthesis of the compounds of this invention is accomplished by displacement of the halogen or tosylate on a halo or tosyl substituted aliphatic acyl anilide by a thiol in the presence of a base. The anilines that are reacted with the acid chloride are readily available to those skilled in the art either as articles of commerce from, for example, Aldrich Chemical Company, Milwaukee, Wis., USA or by synthesis. Addition of a thiol to the double bond of an alkenyl acyl anilide is also a useful synthetic route. Alternatively, the displacement via reaction with a thiol and base, can be carried out on a tosyl or halo substituted aliphatic carboxylic acid or ester which is then converted into the amide via reaction of the corresponding acid chloride with the desired aniline. An ester is preferably hydrolyzed to the corresponding acid before conversion to the acid chloride by, for example, oxalyl chloride. The sulfones and sulfoxides are readily prepared by oxidation of the sulfides with, for example, m-chloroperbenzoic acid or sodium metaperiodate.

Representative anilines include, but are not limited to, 2,6-dimethylaniline, 2,6-diethylaniline, 2-methyl-3-nitroaniline, 4-hexyloxyaniline, 2,4,6-trifluoroaniline, N-ethylaniline, 3-aminobenzonitrile, 4-aminobenzoic acid, 3-hydroxyanthranilic acid, methyl 4-aminobenzoate and the like.

The term "lower alkyl", as used herein, refers to straight or branched chain alkyl groups having from 1 to 6 carbon atoms, inclusive, i.e., methyl, ethyl, n-propyl, iso-propyl, n-butyl, sec-butyl, tert-butyl, n-pentyl, 2-methylbutyl, 2,2-dimethylbutyl, n-hexyl, and the like.

The term "Alk", as used herein, refers to straight or branched chain lower alkylene groups having from 1 to 6 carbon atoms, i.e., methylene, ethylene, n-propylene, iso-propylene, n-butylene, sec-butylene, tert-butylene, n-pentylene, 2-methylbutylene, 2,2-dimethylpropylene, n-hexylene and the like.

The term "halo", as used herein, includes chloro, bromo, iodo and fluoro.

The term "substituted phenyl" refers to phenyl having one or more substituents selected from the group consisting of amino, halo, hydroxy, lower alkyl, lower alkylaminoalkyl, lower dialkylaminoalkyl, trifluoromethyl, lower alkoxy, and the like for $R_4$ and halo, hydroxy, lower alkyl and lower alkoxy for $R_1$ and $R_2$.

The term "lower alkoxy" refers to alkoxy groups having from 1 to 6 straight or branched chain carbon atoms, i.e., methoxy, ethoxy, n-propoxy, tert-butoxy, etc.

Preferred radicals represented by the group of the formula

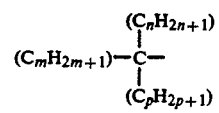

include tertiary alkyl moieties wherein n and m are preferably 1 or 2 and most preferred radical is represented by the group wherein n, m and p are 1, namely t-butyl.

The selective activity of the compounds of this invention was first determined using the following assays.

Test A- An in vitro inhibition of soybean 15-lipoxygenase assay is employed to check the specificity of selected 5-lipoxygenase inhibitors. The oxygen-uptake during the oxidation of arachidonic acid to 15-HPETE by soybean lipoxygenase is measured in the presence and absence of inhibitors, using nordihydroguaiaretic acid (NDGA) as a reference standard. Compounds which inhibit at 100 μM are tested further to determine the $IC_{50}$ values. "IC" stands for "inhibitory concentration".

Test B- Determination of anti-inflammatory, anti-allergy activity: in vitro inhibition of 5-lipoxygenase. The 100,000×g supernatant fraction of Rat Basophilic Leukemia Cell Homogenate (RBL-1) serves as a 5-lipoxygenase enzyme source. The enzyme is incubated with $[1-^{14}C]$-arachidonic acid and $Ca^{++}$ in the presence and absence of test compound. The product of 5-lipoxygenase, 5-hydroxyeicosatetraenoic acid (5-HETE), is separated by thin-layer chromatography and measured by radioactivity. A compound inhibiting 5-HETE synthesis by 30% or more is considered active at that concentration. Initial screening doses are $1 \times 10^{-4}M$. When the compound inhibits more than 50% of 5-HETE synthesis at $10^{-4}M$, that compound is tested at multiple dose levels to determine the $IC_{50}$ value.

Test C- Inhibition of slow reacting substance (SRS) biosynthesis in cells. SRS synthesis by Rat Basophilic Leukemia Cell (RBL-1) cells is induced by incubation of cells with ionophore A23187 alone and in combination with the test compound. The SRS released into the culture media is measured by high pressure liquid chromatography, scintillation counting or bioassay. In the bioassay procedure, the percent inhibition of SRS production is estimated by determining the doses of treated and control media needed in the tissue bath to produce equivalent contractions of segments of isolated guinea pig ileum. A compound that inhibits SRS biosynthesis by 50% or more is considered active at that concentration if an equivalent amount of the compound does not antagonize ileum contraction by SRS directly. If the compound directly inhibits the smooth muscle contractions, it will be considered inactive as an SRS biosynthesis inhibitor. Initial screening doses of test compounds are $1 \times 10^{-4}M$ and $1 \times 10^{-5}M$.

Test-D- In vitro inhibition of human platelet 12-lipoxygenase. A 40,000×g supernatant of platelet lysate is incubated with $[1-^{14}C]$-labeled arachidonic acid in the presence and absence of test compound. The conversion product, 12-hydroxyeicosatetraenoic acid (12-HETE), is quantitated after isolation by thin-layer chromatography. Compounds, initially screened at 100 μM concentration, which inhibit the synthesis of 12-HETE by 30% or more, are considered active. $IC_{50}$ values are determined for active compounds.

Test E-In vitro inhibition of sheep seminal vesicle microsome cyclooxygenase. Arachidonic acid cyclooxygenase reaction rates, in the presence or absence of test compounds, are determined by monitoring oxygen uptake. Compounds which inhibit at $10^{-4}M$ are tested further to determine $IC_{50}$ values.

The following examples further illustrate the present invention.

EXAMPLE 1

Preparation of 3,5-bis(1,1-dimethylethyl)-4-hydroxyphenyl thiocyanate

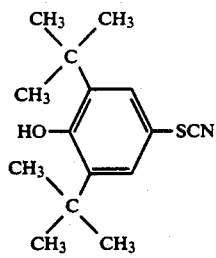

To a three-necked, round bottom 5 L flask, equipped with a mechanical stirrer, gas inlet, thermometer and gas inlet, thermometer and gas outlet, was added 2,6-di-tert-butylphenol (474g, 2.30 mole), ammonium thiocyanate (76.12 g, 4.83 mole) and methanol (1200 ml). The reaction mixture was stirred and cooled to 0° C. in an ice/salt bath. Maintaining the temperature at 0° to 10° C., chlorine gas was slowly bubbled through the mixture for about 1 hour whereupon the reaction mixture was a heterogeneous yellow color. Ammonia was then bubbled through the reaction for about 1½ hours, maintaining the reaction mixture at a temperature of between 0° to 10° C. The reaction was stirred for an additional hour at 0° C., poured into 2 L of cold distilled water and refrigerated overnight. The aqueous phase was decanted and the solid taken up in methanol, precipitated by addition of water, filtered and dried for 2 days over phosphorous pentoxide. The resulting gummy yellow solid was recrystallized from pentane and dried in vacuo to Yield the product as a white powder. m.p. 61.5°–63° C.

Analysis calc. for $C_{15}H_{21}NSO$: Theory: C, 68.40; H, 8.03; N, 5.32; S, 12.17. Found: C, 68.85; H, 8.05; N, 5.29; S, 12.12.

EXAMPLE 2

Preparation of 2,6-bis(1,1-dimethylethyl)-4-mercaptophenol

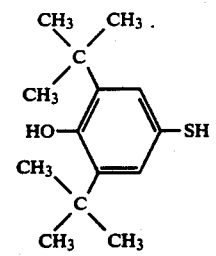

3,5-bis(1,1-Dimethylethyl)-4-hydroxyphenyl thiocyanate (55 g, 0.209 mole) was dissolved in acetone (200 ml) under an argon atmosphere. Water (7.6 g, 0.42 mole) was added and the reaction cooled to 0° C. Triethylphosphine (24.7 g, 0.209 mole) was added dropwise over a period of 1 hour and the reaction was then allowed to warm to room temperature with stirring. The solution was concentrated, solvents removed, and the resulting oil purified by chromatography on silica. The fractions containing the thiol were combined, the solvents removed to yield a white powder which was recrystallized from methanol/water and dried to yield 43.3 g of the desired product. NMR confirmed the identity of the product.

EXAMPLE 3

Preparation of N-(2,6-dimethylphenyl)-2-propenamide

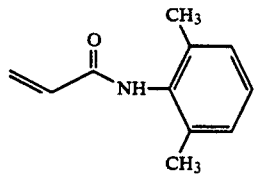

A mixture of 2,6-dimethylaniline (8.68 g, 0.0718 mole) and triethylamine (15.3 ml) in ethyl ether (250 ml) was cooled to +5° C. A solution of acryloyl chloride (6.47 g, 0.0716 mole) in ethyl ether (25 ml) was added dropwise with stirring over a 20 minute period. The solution was allowed to warm to room temperature and stirred for 72 hours. 10 Percent hydrochloric acid (150 ml) was added and the layers separated. The acid layer was extracted with ethyl acetate (150 ml), combined, washed with water (150 ml), dried over sodium sulfate, filtered and the solvents evaporated. The solid was taken up in hot ethyl acetate and recrystallized from hexane to yield the title compound, m.p. ca. 143.5°–145.0° C.

Analysis calc. for $C_{11}H_{13}NO$ (175.23)i Calc.: C, 75.40; H, 7.48; N, 7.99. Found: C, 75.25; H, 7.51; N, 7.79.

EXAMPLE 4

Preparation of 3-[[3,5-bis(1,1-dimethylethyl)-4-hydroxyphenyl]thio]-N-(2,6-dimethylphenyl)propanamide

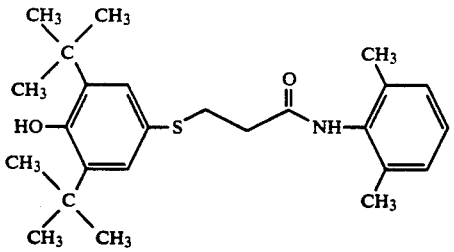

2,6-bis-(1,1-Dimethylethyl)-4-mercaptophenol(1.19 g, 0.005 mole), N-(2,6-dimethylphenyl)-2-propenamide (0.87 g, 0.005 mole) and triethylamine (0.5 ml) in methanol (100 ml) were stirred at room temperature under argon for 12 hours. The solvent and triethylamine were removed on a rotary evaporator and the product purified by chromatography on silica. The solvents were removed and the product recrystallized from ethyl acetate/hexane, filtered and dried in vacuo to yield the title compound, m.p. ca. 142.5°–144° C.

Analysis calc.: for $C_{25}H_{35}NSO_2$(413.62): Calc.: C, 72.60; H, 8.53; S, 7.75; N, 3.39. Found: C, 72.28; H, 8.75; S, 7.80; N, 3.37.

EXAMPLE 5

Preparation of N-(2,6-diethylphenyl)-2-propenamide

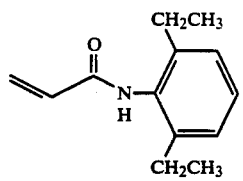

To a cold solution of 2.6-diethylaniline (60.6 g, 0.07 mole) in ethyl acetate (600 ml) was added a solution of acryloyl chloride (45.2 g, 0.5 mole) in ethyl acetate (50 ml) over a 30 minute period. The ice bath was removed and the solution stirred for 4 hours. 10 Percher hydrochloric acid was added and the solution stirred gently for 15 minutes. The layers were separated and the organic layer washed with water, dried over sodium sulfate, filtered and the solvents removed on a rotary evaporator leaving an orange solid. The solid was recrystallized from ethyl acetate/hexane and the product filtered and dried.

Analysis calc. for $C_{13}H_{17}NO$(203.28): Calc.: C, 76.81; H, 8.43; N, 6.89. Found: C, 77.00; H, 8.38; N, 6.83.

EXAMPLE 6

Preparation of 3-[[3,5-bis(1,1-dimethylethyl)-4-hydroxyphenyl]thio]-N-(2,6-diethylphenyl)propanamide

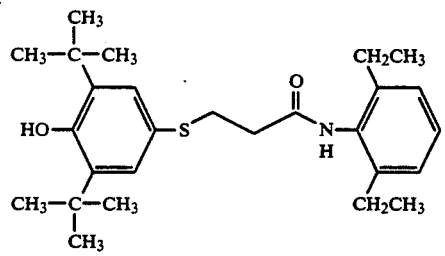

The title compound was prepared by the method of Example 4 from N-(2,6-diethylphenyl)-2-propenamide (1.01 g, 0.005 mole), 2,6-bis(1,1-dimethylethyl)-4-mercaptophenol (1.19 g, 0.005 mole) and triethylamine (0.5 ml) in methanol, m.p. ca. 150.5°–151.5° C.

Analysis calc. for $C_{27}H_{39}N_2O$ (441.67): Calc.: C, 73.43; H, 8.90; N, 3.17; S, 7.26. Found: C, 73.38; H, 8.97; N, 3.19; S, 7.35.

EXAMPLE 7

Preparation of 3-[[3,5-bis(1,1-dimethylethyl)-4-hydroxyphenyl]sulfinyl]-N-(2,6-dimethylphenyl)propanamide

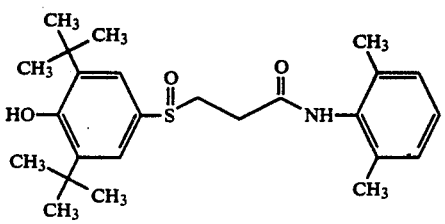

The title compound of Example 4 (0.5 g, 0.0012 mole) was dissolved in methylene chloride (20 ml) under argon and cooled to 0° C. m-Chloroperbenzoic acid (0.257 g, 0.0012 mole) dissolved in methylene chloride (10 ml) was slowly added with stirring and the solution stirred for 12 hours. The product was purified by chromatography on silica. The solvents were removed on a rotary evaporator, and the product dried and recrystallized from hexane, m.p. ca. 162.5°–164.5° C.

Analysis calc. for $C_{25}H_{35}NSO_3$(429 62): Calc.: C, 69.89; H, 8.21; N, 3.26; S, 7.46. Found: C, 69.60; H, 8.13; N, 3.15; S, 7.52.

EXAMPLE 8

Preparation of 3-[[3,5-bis(1,1-dimethylethyl)-4-hydroxyphenyl]sulfonyl]-N-(2,6-dimethylphenyl)propanamide

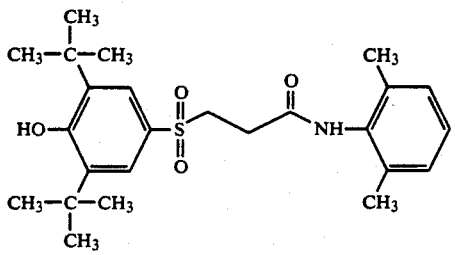

Following the procedure of Example 7, the title compound of Example 4 (0.15 g, 0.00036 mole), m-chloroperbenzoic acid (0.154 g, 0.0072 mole) in methylene chloride (10 ml) were stirred under argon for 12 hours. The solution was washed well with sodium bicarbonate, dried, concentrated and the product purified by chromatography on silica and recrystallized from hexane, m.p. 217.5°–219° C.

Analysis calc. for $C_{25}H_{35}NSO_4$(445.60): Calc.: C, 67.38; H, 7.92; N, 3.14; S, 7.19. Found: C, 67.19; H, 8.00; N, 3.06; S, 7.11.

EXAMPLE 9

Preparation of 4-[[3,5-bis(1,1-dimethylethyl)-4-hydroxy phenylthiobutanoic acid

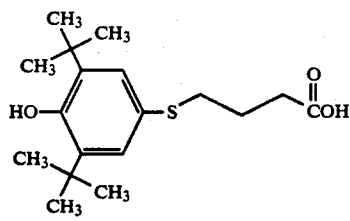

Potassium hydroxide flakes (2.52 g, 0.005 mole) were added to a clear solution of 2,6-bis(1,1-dimethylethyl)-4-mercaptophenol (3.57 g, 0.015 mole) and ethyl-4-bromobutyrate (3.23 g, 0.0165 mole) in acetone (100 ml). Water (20 ml) was added and the solution stirred for 1.5 hours, the solvent removed on a rotary evaporator and water (50 ml) added. The organic layer was extracted with ethyl ether (3×75 ml). The aqueous layer was acidified with concentrated hydrochloric acid, extracted with ethyl ether (2×50 ml), washed with water (50 ml), dried over sodium sulfate, filtered and the solvents removed, leaving an oil, which was purified by chromatography on silica. The product was recrystallized from ethyl ether/Skellysolve B, filtered and the product dried in vacuo at room temperature for 12 hours, m.p. ca. 112°–113.5° C.

Analysis calc. for $C_{18}H_{28}O_3S$(324.48): Calc.: C, 66.63; H, 8.70; S, 9.88. Found: C, 66.71; H, 8.74; S, 9.57.

EXAMPLE 10

Preparation of 4-[[3,5-bis(1,1-dimethylethyl)-4-hydroxyphenyl]thio]-N-(2,6-dimethylphenyl)butanamide

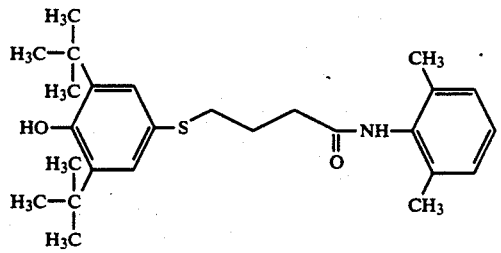

The title compound of Example 9 (1.53 g, 0.0047 mole) was dissolved in benzene (50 ml) and the solution cooled to approximately 5° C. in an ice bath. A solution of oxalyl chloride in benzene (20 ml) was added dropwise over 5 minutes. The ice bath was removed and the solution allowed to warm to room temperature and stirred for 5 hours. The benzene was evaporated, fresh benzene (50 ml) added, and 2,6-dimethylaniline (0.61 g, 0.0050 mole) and triethylamine (1 ml) was added and the solution stirred overnight. The benzene was evaporated, ethyl ether (50 ml) added and the solid (triethylamine hydrochloride) filtered and the filtrate concentrated to an oil. The product was purified by chromatography on silica and recrystallized from hexane, m.p. 139.5°–140.5° C. Analysis calc. for $C_{26}H_{37}NO_2S$(427.64): Calc.: C, 73.02; H, 8.72; S, 7.50; N, 3.28. Found: C, 73.21; H, 8.93; S, 7.57; N, 3.50.

EXAMPLE 11

Preparation of 2-[[3,5-bis(1,1-dimethylethyl)-4-hydroxyphenylthio]-pentanoic acid

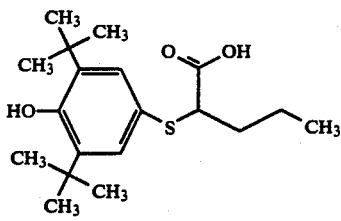

The title compound was prepared according to the method of Example 9 from potassium hydroxide flakes (3.36 g, 0.06 mole), 2,6-bis(1,1-dimethylethyl)-4-mercaptophenol (4.76 g, 0.02 mole) and ethyl-2bromovalerate (4.18 g, 0.02 mole) in acetone (100 ml). The structure was confirmed by NMR.

EXAMPLE 12

Preparation of 2-[[3,5-bis(1,1-dimethylethyl)-4-hydroxyphenyl]thio]-N-(2,6-dimethylphenyl)pentanamide

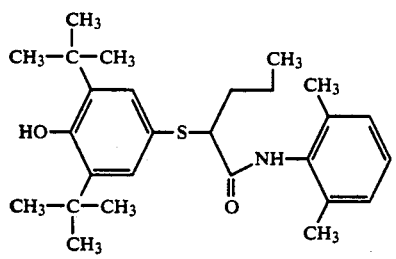

The title compound of Example 11 (2.3 g, 0.0068 mole) was dissolved in benzene and the solution cooled to 10° C. in an ice bath. A solution of oxalyl chloride (1.14 g, 0.009 mole) in benzene (10 ml) was added dropwise over a period of 20 minutes. The ice bath was removed and the solution stirred at room temperature for 12 hours. The benzene was removed, fresh benzene (10 ml) added and the procedure repeated. The residue was taken up in benzene and a solution of 2,6-dimethylaniline (0.84 g, 0.007 mole) in benzene (25 ml) added over a period of 20 minutes, followed by the dropwise addition of a solution of triethylamine (1 ml). The solution was stirred for 4 hours and the benzene removed. The residue was taken up in ethyl ether (100 ml), stirred, and the white solid filtered. The filtrate was stripped and the product purified by chromatography on silica. The product was recrystallized from ethyl acetate/hexane, filtered and dried, m.p. ca. 137°–139.5° C.

Analysis calc. for $C_{27}H_{39}NO_2S(441.67)$: Calc.: C, 73.43; H, 8.90; N, 3.17; S, 7 26. Found: C, 73.75; H, 8.90; N, 3.12; S, 7.41.

EXAMPLE 13

Preparation of 2-chloro-N-(2,6-dimethylphenyl)acetamide

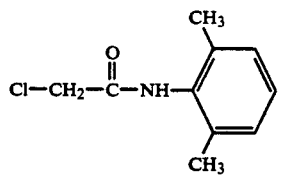

Chloroacetyl chloride (4.0 g) in methylene chloride (25 ml) was cooled via an ice bath to 0° C. A solution of 2,6-dimethylaniline (4.25 g) and triethylamine (5 ml) in methylene chloride (25 ml) was added dropwise over 1 hour and the resulting solution stirred and allowed to come to room temperature for a 20 hour period. 10% Hydrochloric acid was added and the layers were separated. The organic layer was washed with 1N hydrochloric acid and water, dried over sodium sulfate, filtered and the solvent removed to give a solid which was recrystallized from benzene. The structure was confirmed by NMR.

EXAMPLE 14

Preparation of 2-[[3,5-bis(1,1-dimethylethyl)-4-hydroxyphenyl]thio]-N-(2,6-dimethylphenyl)acetamide

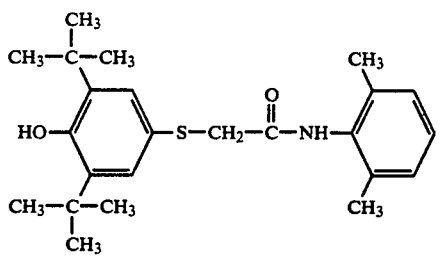

The title compound was prepared by dissolving 2-chloro-N-(2,6-dimethylphenyl)acetamide (1.8 g, 0.0091 mole) and 2,6-bis(1,1-dimethylethyl)-4-mercaptophenol (2.17 g, 0.0091 mole) in acetonitrile (20 ml) under argon. Triethylamine (1.25 ml) was added and the solution stirred at room temperature under argon for 12 hours. The solution was acidified with 10% hydrochloric acid with stirring, extracted with ethyl acetate (3×), the extracts combined, washed with water and dried over sodium sulfate. The solvent was removed on a rotary evaporator and the product purified by chromatography over silica and recrystallized from ethyl acetate/benzene. m.p. ca. 137.7° C.

Analysis calc. for $C_{24}H_{33}NO_2S(399.59)$: Calc.: C, 72.14; H, 8.32; N, 3.51. Found: C, 72.47; H, 8.57; N, 3.48.

EXAMPLE 15

Preparation of 3,5-dichloro-4-hydroxyphenyl thiocyanate

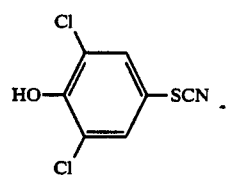

2,6-Dichlorophenol (100 g, 0.613 mole) and ammonium thiocyanate (102.73 g, 1.350 mole) were mixed in methanol and the solution cooled to 0° C. Chlorine gas was bubbled through the reaction, maintaining the temperature below 10° C. The solution turned a pale yellow color. The reaction was stirred for a total of 3 hours until acidic, at which time ammonia gas was bubbled through and the solution stirred for an additional three hours at 0° to 10° C. The reaction was poured into iced distilled water, and filtered, yielding approximately 20 g of a yellow solid which was dried over night in vacuo. The filtrate was extracted with ethyl acetate, dried over magnesium sulfate and stripped to yield approximately 100 g of crude product. Following purification by chromatography, the material was taken up in 1 liter of toluene, charcoal was added, stirred, filtered, and recrystallized from hexane to yield 55.03 g of product as a yellow solid. The structure was confimed by NMR.

EXAMPLE 16

Preparation of 2,6-dichloro-4-mercaptophenol

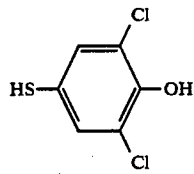

The title compound of Example 15 (55.03 g, 0.25 mole) was dissolved in 300 ml of acetone. Water (4.5 ml, 0.25mole) was added and the solution cooled to 0° C. Triethylphosphine (36.9 ml, 0.250mole) was added dropwise over a period of 65 minutes, maintaining the temperature at 0° C. The reaction was allowed to warm to room temperature, stirred for 1½ hours, the solvent was removed and the product purified by chromatography. Analysis Calcd. for $C_6H_4OCl_2S$(195.98): Calcd.: C, 36.94; H, 2.07; Cl, 36.35; S, 16.44. Found: C, 36.96; H, 2.06; Cl, 36.31; S, 16.56.

EXAMPLE 17

Preparation of 2'-hydroxyl[1,1':3', 1''-terphenyl5'-yl thiocyanate

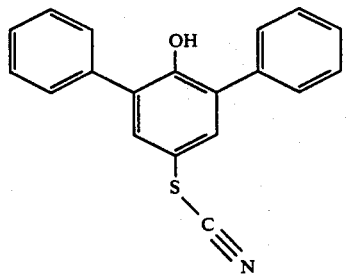

2,6-Diphenylphenol (100 g, 0.406 mole) and ammonium thiocyanate (67.99 g, 0.893 mole) were suspended in methanol (150 ml) in a three necked round bottom flask equipped with magnetic stirrer, thermometer and bubbler. The reaction mixture was cooled to −5° C. in an acetone/ice bath and chlorine gas bubbled through the solution for three hours. Maintaining the temperature below 10° C., ammonia gas was bubbled through the reaction for 2 hours. The contents of the flask were then pured into iced distilled water (250 ml) and allowed to stand for 12 hours. After filtering, the solid was dried in vacuo at 45° C. for 12 hours. The title compound was purified by chromatography on silica and recrystallized from hexane, m.p. ca. 104°–106.5° C.

Analysis calc. for $C_{19}H_{13}OSN$(303 69): Calc.: C. 75.22; H, 4.32; N, 4.62; S, 10.57. Found: C, 75.12; H, 4.49; N, 4.65; S, 10.41.

EXAMPLE 18

Preparation of 5'-mercapto-[1,1':3',1''-terphenyl]-2'-ol

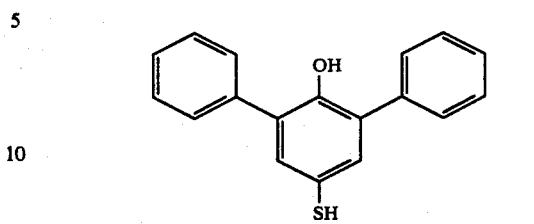

The title compound of Example 17 (32.2 g, 0.106 mole) and water (1.9 ml) were dissolved in acetone (150 ml) with stirring and cooled to −5° C. Triethylphosphine (15.7 ml, 0.106 mole) was added dropwise over a period of 40 minutes. The reaction was stirred at 0° C. for 1 hour and then at room temperature for 2 hours. The solvent was evaporated and the product isolated by chromatography on silica.

Analysis calc. for $C_{18}H_{14}OS$ (278 31): Calc. C, 77 67; H, 5 07; S, 11.52 Found: C, 77 80; H 5 19; S, 11.68.

EXAMPLES 19-34

By replacing 2,6-bis-(1,1-dimethylethyl)-4-mercaptophenol with the thiol of Examples 16 or 18, the following compounds are obtained.

Example 19. 3-[(3,5-dichloro-4-hydroxyphenyl) thio]-N-(2,6-dimethylphenyl)propanamide.

Example 20. 3-[(3,5-dichloro-4-hydroxyphenyl) thio-N-(2,6-diethylphenyl)propanamide.

Example 21. 3-[(3,5-dichloro-4-hydroxyphenyl) sulfinyl]-N-(2,6-dimethylphenyl)propanamide.

Example 22. 3-[(3,5-dichloro-4-hydroxyphenyl) sulfonyl]-N-(2,6-dimethylphenyl)propanamide.

Example 23. 4-[(3,5-dichloro-4-hydroxyphenyl) thio-N-(2,6-dimethylphenyl)butanamide.

Example 24. 2-[(3,5-dichloro-4-hydroxyphenyl) thio]-N-(2,6-dimethylphenyl)pentamide.

Example 25. 2-[(3,5-dichloro-4-hydroxyphenyl) thio]-N-2,6-diethylphenyl)acetamide.

Example 26. 2-[(3,5-dichloro-4-hydroxyphenyl) thio]-N-(2,6-dimethylphenyl)acetamide.

Example 27. 3-[(2'-hydroxy[1,1',3',1''-terphenyl]-5'-yl)thio-N-(2,6-dimethylphenyl)propanamide.

Example 28 3-(2'-hydroxy[1,1',3',1''-terphenyl-5'-yl)-thio]-N-(2,6-diethylphenyl)propanamide.

Example 29. 3-[(2'-hydroxy[1,1':3',1''-terphenyl -5'-yl)sulfinyl]-N-(2,6-dimethylphenyl)propanamide.

Example 30. 3-[(2'-hydroxy[1,1':3',1''-terphenyl]-5'-yl)-sulfonyl]-N-(2,6-dimethylphenyl)propanamide.

Example 31. 4-[(2'-hydroxy[1,1':3',1''-terphenyl]-5'-yl)-thio]-N-(2,6-dimethylphenyl)butanamide.

Example 32. 2-[(2'-hydroxy[1,1':3',1''-terphenyl]-5'-yl)-thio]-N-(2,6-dimethylphenyl)pentanamide.

Example 33. 2-[(2'-hydroxy[1,1':3',1''-terphenyl]-5'-yl)-thio]-N-(2,6-diethylphenyl)acetamide.

Example 34. 2-[(2'-hydroxy[1,1':3',1''-terphenyl]-5'-yl)-thio]-N-(2,6-dimethylphenyl)acetamide.

EXAMPLES 35-37

By substituting other anilines in N-(2,6-dimethylphenyl)-2-propenamide, N-(2,6-diethylphenyl)-2propenamide, N-(2,6- dimethylphenyl)-2-acetamide, etc., the following representative compounds are obtained:

Example 35. 3-[(3.5-dichloro-4-hydroxyphenyl)thio]-N-(2,4,6-trifluorophenyl)propanamide from 2,4,6-trifluoroaniline;

Example 36. 3-[(3,5-dichloro-4-hydroxyphenyl) thio]-N-(4-hexyloxyphenyl)propanamide from 4-hexyloxyaniline;

Example 37. 3-[(3.5-dichloro-4-hydroxyphenyl) sulfinyl]-N-(3-aminophenyl)propanamide from 3-aminoaniline; and the like.

EXAMPLE 38

Preparation of
[[3,5-bis(1,1-dimethylethyl)-4-hydroxyphenyl]thio]-N-(2,6-dichlorophenyl)acetamide

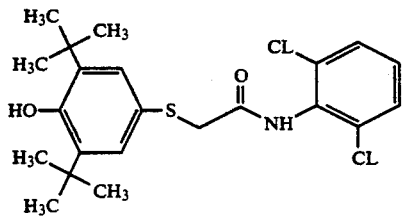

Following the procedure of Example 14, utilizing 2-chloro- N-(2,6-dichlorophenyl)acetamide in lieu of 2-chloro-N-(2,6-dimethylphenyl)acetamide the title compound, m.p. ca. 168°–170° C.

Analysis calc. for $C_{22}H_{27}Cl_2NO_2S$ Calc C, 59.99; H, 6.18; N, 3.18; S, 7.28. Found: C, 60.19; H, 6.30; N, 3.01; S, 7.39.

The active agents of this invention can be administered to animals, including humans, as pure compounds. However, it is advisable to first combine one or more of the active compounds with one or more suitable pharmaceutically acceptable carriers or diluents to attain a satisfactory size to dosage relationship and thereby obtain a pharmaceutical composition.

Pharmaceutical carriers which are liquid or solid can be employed. Solid carriers such as starch, sugars, talc and the like can be used to form powders which may be used for direct administration or to fill gelatin capsules. Suitable lubricants such as magnesium stearate, stearic acid, as well as binders and disintegrating agents may be included to form tablets. Additionally, flavoring and sweetening agents may be added.

Unit dosage forms such as tablets and capsules can contain any suitable, predetermined, therapeutically effective amount of one or more active agents and a pharmaceutically acceptable carrier or diluent. Generally speaking, solid oral unit dosage forms of a compound of this invention will contain from 1.75 to 750 mg per tablet of drug.

The compounds of this invention exhibit both oral and parenteral activity and accordingly can be formulated in dosage forms for either oral or parenteral administration.

Solid oral dosage forms include capsules, tablets, pills, powders, granules and the like.

Liquid dosage forms for oral administration include emulsions, suspensions, solutions, syrups and the like containing diluents commonly used in the art such as water. Besides inert diluents, such preparations can also include adjuvants such as wetting agents, emulsifying and suspending agents, and sweetening, flavoring and perfuming agents.

Preparations for parenteral administration include sterile aqueous or non-aqueous solutions. Examples of nonaqueous solvents or vehicles are propylene glycol, polyethylene glycol, vegetable oils such as olive oil and injectable organic esters such as ethyl oleate. The parenteral preparations are sterilized by conventional methods.

The compounds of this invention may also be formulated for topical or transdermal application using carriers which are well known in the art, as well as in aerosols or sprays for nasal administration.

The amount of active ingredient administered may be varied; however, it is necessary that the amount of active ingredient be such that a suitable dosage is given. The selected dosage depends upon the desired therapeutic effect, the route of administration and the duration of treatment. Generally speaking, oral dosages of from 0.1 to 100 mg/kg, and preferably from 0.5 to 50 mg/kg of body weight daily are administered to patients in need of such treatment, preferably in divided dosages, e.g. three to four times daily. In the case of acute allergic or hypersensitivity reactions, it is generally preferable to administer the initial dosage via the parenteral route, e.g. intravenous, and continue parenteral administration until the patient is stabilized, and can be maintained, if necessary on oral dosing.

In the case of psoriasis and other skin conditions, it is preferred to apply a topical preparation of a compound of this invention to the affected areas three or four times daily.

In treating asthma and arthritis with a compound of this invention, the compounds may be administered either on a chronic basis, or as symptoms appear. However, in the case of arthritis and other inflammatory conditions which can lead to deterioration of joints and malformations, it is generally preferable to administer the active agent on a chronic basis.

When the compounds of this invention are coadministered with one or more cyclooxygenase inhibitors, they may conveniently be administered in a unit dosage form or may be administered separately. When the patient is allergic or hypersensitive to the cycloxygenase inhibitor, it is preferred to initiate therapy with a compound of this invention prior to administration of the cyclooxygenase inhibitor.

A typical tablet of this invention can have the following composition:

| Ingredient | Mg/tablet |
| --- | --- |
| Active ingredient | 100 |
| Starch, U.S.P. | 57 |
| Lactose, U.S.P. | 73 |
| Talc, U.S.P. | 9 |
| Stearic acid | 12 |

It will be understood by those skilled in the art that the above examples are illustrative, not exhaustive, and that modifications may be made without departing from the spirit of the invention and the scope of the claims.

The invention claimed is:

1. A compound of the formula:

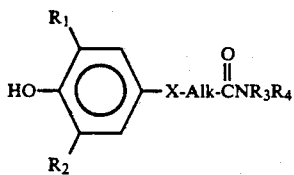

wherein $R_1$ and $R_2$ are 1,1-dimethylethyl; X is thio; Alk is straight or branched chain lower alkylene having from 1 to 6 carbon atoms; $R_3$ is hydrogen; and $R_4$ is 2,6-dimethyl or 2,6-diethyl substituted phenyl.

2. A pharmaceutical composition for the treatment of inflammation and allergic reactions comprising a therapeutically effective amount of a compound of the formula

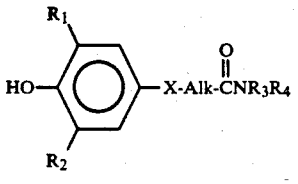

wherein $R_1$ and $R_2$ are 1,1-dimethylethyl; X is thio; Alk is straight or branched chain lower alkylene having from 1 to 6 carbon atoms; $R_3$ is hydrogen; and $R_4$ is 2,6-dimethyl or 2,6-diethyl substituted phenyl; and a pharmaceutically acceptable carrier or diluent.

3. A compound of the formula

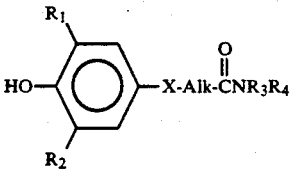

wherein $R_1$ and $R_2$ are 1,1-dimethylethyl; X is thio; Alk is straight chain lower alkylene having from 1 to 6 carbon atoms; $R_3$ is hydrogen; and $R_4$ is 2,6 dimethyl or 2,6-diethyl substituted phenyl.

4. A compound according to claim 3 wherein Alk is ethylene.

5. A pharmaceutical composition for the treatment of inflammation and allergic reactions comprising a therapeutically effective amount of a compound of the formula

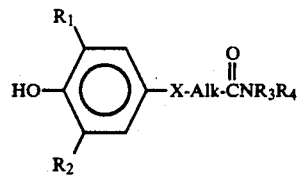

wherein $R_1$ and $R_2$ are 1,1-dimethylethyl; X is thio; Alk is straight chain lower alkylene having from 1 to 6 carbon atoms; $R_3$ is hydrogen; and $R_4$ is 2,6 dimethyl or 2,6-diethyl substituted phenyl; and a pharmaceutically acceptable carrier or diluent.

6. A pharmaceutical composition according to claim 5 wherein Alk is ethylene.

7. A pharmaceutical composition according to claim 6 wherein said compound is 3-[[3,5-bis(1,1-dimethylethyl)-4-hydroxyphenyl]thio]-N-(2,6-dimethylphenyl)-propanamide.

8. A pharmaceutical composition according to claim 6 wherein said compound is 3-[[3,5-bis(1,1-dimethylethyl)-4-hydroxyphenyl]thio]-N-(2,6-diethylphenyl)-propanamide.

9. A compound of claim 4, 3-[[3,5-bis(1,1-dimethylethyl-4-hydroxyphenyl]thio]-N-(2,6-dimethylphenyl)propanamide.

10. A compound of claim 4, 3-[[3,5-bis(1,1-dimethylethyl)-4-hydroxyphenyl]thio]-N-(2,6-diethylphenyl)-propanamide.

11. A compound of claim 1, 4-[[3,5-bis(1,1-dimethylethyl)-4-hydroxyphenyl]thio]-N-(2,6-dimethylphenyl)-butanamide.

12. A compound of claim 1, 2-[[3,5-bis(1,1-dimethylethyl)-4-hydroxyphenyl]thio]-N-(2,6-dimethylphenyl)-pentamide.

13. A compound of claim 1, 2-[[3,5-bis(1,1-dimethylethyl)-4-hydroxyphenyl]thio]-N-(2,6-dimethylphenyl)acetamide.

* * * * *

UNITED STATES PATENT AND TRADEMARK OFFICE
CERTIFICATE OF CORRECTION

PATENT NO. : 5,225,444
DATED : July 6, 1993
INVENTOR(S) : Mueller, et al.

It is certified that error appears in the above-indentified patent and that said Letters Patent is hereby corrected as shown below:

Column 1, line 13, reading "Jul. 27, 1990, now abandoned is a related case." should read -- Jul. 27, 1990, is a related case.

Column 3, line 3, reading "and hence and represent" should read -- and hence represent --.

Column 3, line 37, reading "R1 and R2" should read -- $R_1$ and $R_2$ --.

Column 3, line 55, reading "joint disease, asthma/" should read -- joint disease, asthma, --.

Column 7, line 34, reading "$C_{11}H_{13}NO(175.23)i$" should read -- $C_{11}H_{13}NO(175.23)$: --.

Column 8, line 13, reading "2,6-diethylaniline (60.6 g, 0.07 mole)" should read -- 2,6-diethylaniline (60.6 g, 0.407 mole) --.

Column 8, line 17, reading "10 Percher" should read -- 10 Percent --.

UNITED STATES PATENT AND TRADEMARK OFFICE
CERTIFICATE OF CORRECTION

PATENT NO. : 5,225,444
DATED : July 6, 1993
INVENTOR(S) : Mueller, et al.

It is certified that error appears in the above-indentified patent and that said Letters Patent is hereby corrected as shown below:

Column 9, line 55, reading "(2.52 g, 0.005 mole)" should read -- (2.52 g, 0.045 mole) --.

Column 10, line 65, reading "ethyl-2bromovalerate" should read -- ethyl-2-bromovalerate --.

Column 11, line 20, reading "to 10°C." should read -- to +10°C. --.

Column 13, line 59, reading "then pured into" should read -- then poured into --.

Column 13, line 65, reading "(303 69):" should read -- (303.69): --.

Column 14, line 22, reading "Calc. C, 77 67; H, 5 07;" should read -- Calc. C, 77.67; H, 5.07; --.

Column 14, line 23, reading "Found: C, 77 80; H 5 19;" should read -- Found: C, 77.80; H, 5.19; --.

Column 14, line 32, reading "thio-N-" should read -- thio]-N- --.

Column 14, line 46, reading "[1,1',3',1"-" should read -- [1,1':3',1"- --.

Column 14, line 48, reading "3-(2'-hydroxy[1,1',3',1"-" should read -- 3-[(2'-hydroxy[1,1':3',1"- --.

Column 14, line 66, reading "2propenamide," should read -- 2-propenamide, --.

UNITED STATES PATENT AND TRADEMARK OFFICE
CERTIFICATE OF CORRECTION

PATENT NO. : 5,225,444
DATED : July 6, 1993
INVENTOR(S) : Mueller, et al.

It is certified that error appears in the above-indentified patent and that said Letters Patent is hereby corrected as shown below:

Column 15, line 13, reading "[[3,5-bis" should read -- 2-[[3,5-bis --.

Column 15, line 29, reading "Calc C, 59.99;" should read -- Calc.: C, 59.99; --.

Signed and Sealed this

Twentieth Day of December, 1994

Attest:

BRUCE LEHMAN

Attesting Officer    Commissioner of Patents and Trademarks